United States Patent
Li et al.

(10) Patent No.: US 11,419,866 B2
(45) Date of Patent: Aug. 23, 2022

(54) PHARMACEUTICAL COMPOSITION FOR SUSTAINED RELEASE DELIVERY OF BUPRENORPHINE

(71) Applicant: Foresee Pharmaceuticals Co., Ltd., Taipei (TW)

(72) Inventors: Yuhua Li, Landenberg, PA (US); MingHsin Li, Taipei (TW); Chen-Chang Lee, New Taipei (TW); Chia-Ying Yang, New Taipei (TW); Chih-Ying Lin, Yilan (TW)

(73) Assignee: Foresee Pharmaceuticals Co., Ltd., Taipei (TW)

(*) Notice: Subject to any disclaimer, the term of this patent is extended or adjusted under 35 U.S.C. 154(b) by 0 days.

(21) Appl. No.: 16/962,040

(22) PCT Filed: Jan. 21, 2019

(86) PCT No.: PCT/US2019/014422
§ 371 (c)(1),
(2) Date: Jul. 14, 2020

(87) PCT Pub. No.: WO2019/144079
PCT Pub. Date: Jul. 25, 2019

(65) Prior Publication Data
US 2020/0345724 A1 Nov. 5, 2020

Related U.S. Application Data

(60) Provisional application No. 62/620,317, filed on Jan. 22, 2018.

(51) Int. Cl.
*A61K 31/485* (2006.01)
*A61K 47/12* (2006.01)
(Continued)

(52) U.S. Cl.
CPC ........... *A61K 31/485* (2013.01); *A61K 47/12* (2013.01); *A61K 47/183* (2013.01); *A61K 47/20* (2013.01); *A61K 47/22* (2013.01); *A61K 47/42* (2013.01)

(58) Field of Classification Search
CPC .... A61K 31/485; A61K 47/10; A61K 9/0019; A61K 9/06; A61K 47/22; A61K 47/20;
(Continued)

(56) References Cited

U.S. PATENT DOCUMENTS 4,626,539 A  12/1986 Aungst et al.
8,236,755 B2  8/2012 Thuresson et al.
(Continued)

FOREIGN PATENT DOCUMENTS

EP  0368409 A2 * 5/1990 .......... A61K 31/485
GB  2100985 * 1/1983
(Continued)

OTHER PUBLICATIONS

International Application No. PCT/US2019/014422, International Search Report and Written Opinion dated Apr. 11, 2019, 11 pages.
(Continued)

*Primary Examiner* — Lezah Roberts
(74) *Attorney, Agent, or Firm* — MagStone Law, LLP; Enshan Hong

(57) ABSTRACT

The present invention is directed to a depot composition for sustained release delivery of buprenorphine with enhanced stability and bioavailability. The composition is an injectable, low viscosity liquid and can form a depot in situ capable of delivering therapeutic level of buprenorphine over a period of time from one week to 3 months.

10 Claims, 4 Drawing Sheets

Color stabilizing effect of antioxidant in buprenorphine formulation at 60°C for 14 days

(51) Int. Cl.
  *A61K 47/18*    (2017.01)
  *A61K 47/20*    (2006.01)
  *A61K 47/22*    (2006.01)
  *A61K 47/42*    (2017.01)

(58) Field of Classification Search
  CPC ......... A61K 47/12; A61K 47/44; A61P 25/36;
                                          A61P 25/04
  See application file for complete search history.

(56) References Cited

U.S. PATENT DOCUMENTS

2007/0116730 A1*  5/2007  Simmons ............... A61P 25/04
                                                  424/400
2012/0178771 A1   7/2012  Babul et al.
2017/0079974 A1   3/2017  Zhou et al.

FOREIGN PATENT DOCUMENTS

WO       2007061739  A2    5/2007
WO       2012031252  A1    3/2012

OTHER PUBLICATIONS

European Application No. 19741052.5,Extended European Search Report dated Aug. 19, 2021, 7 pages.
International Application No. PCT/US2019/014422, International Preliminary Report dated Jul. 28, 2020, 8 pages.

* cited by examiner

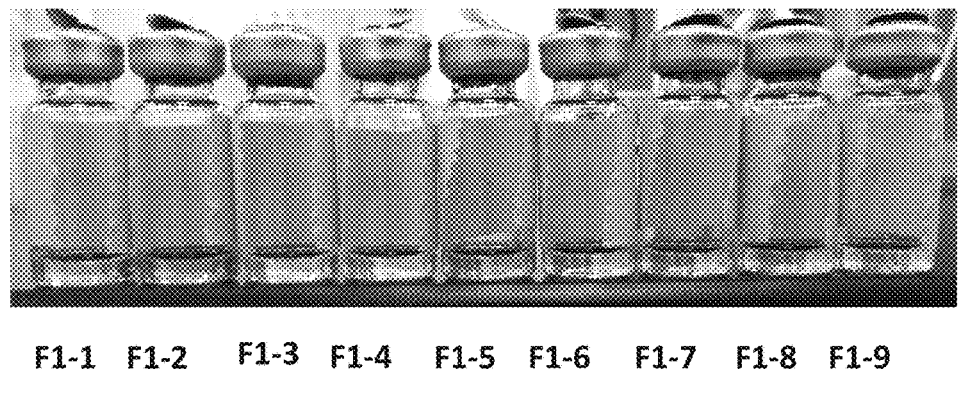
Figure 1. Color stabilizing effect of antioxidant in buprenorphine formulation at 60°C for 14 days
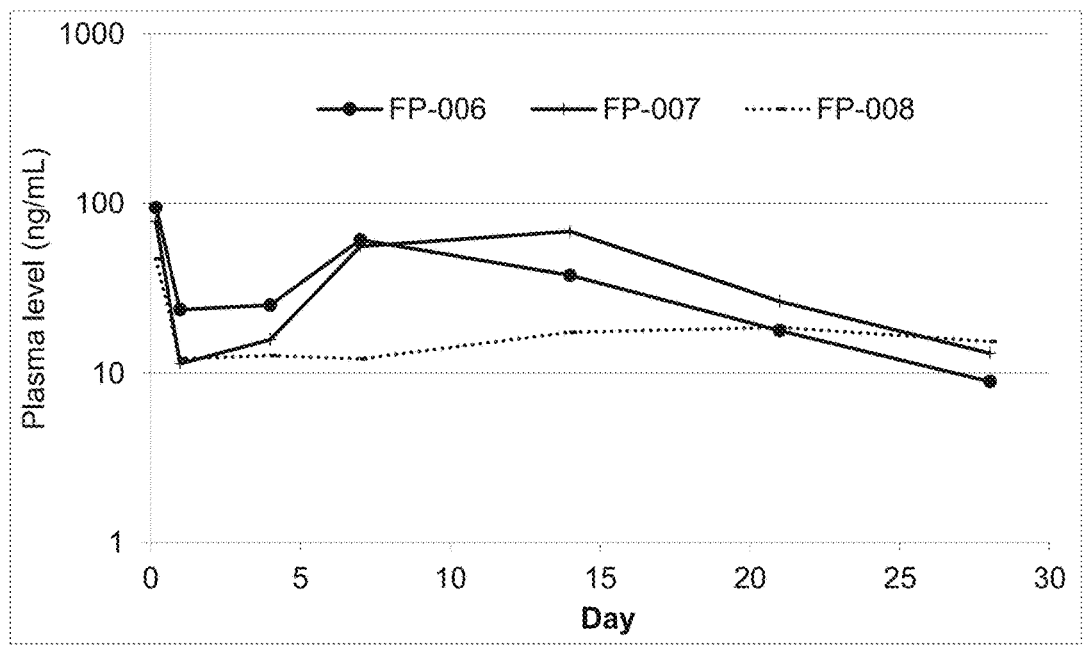
Figure 2. PK profiles of buprenorphine formulations, FP-006 to FP-008, administered subcutaneously with 75mg/kg dose level (N=5).

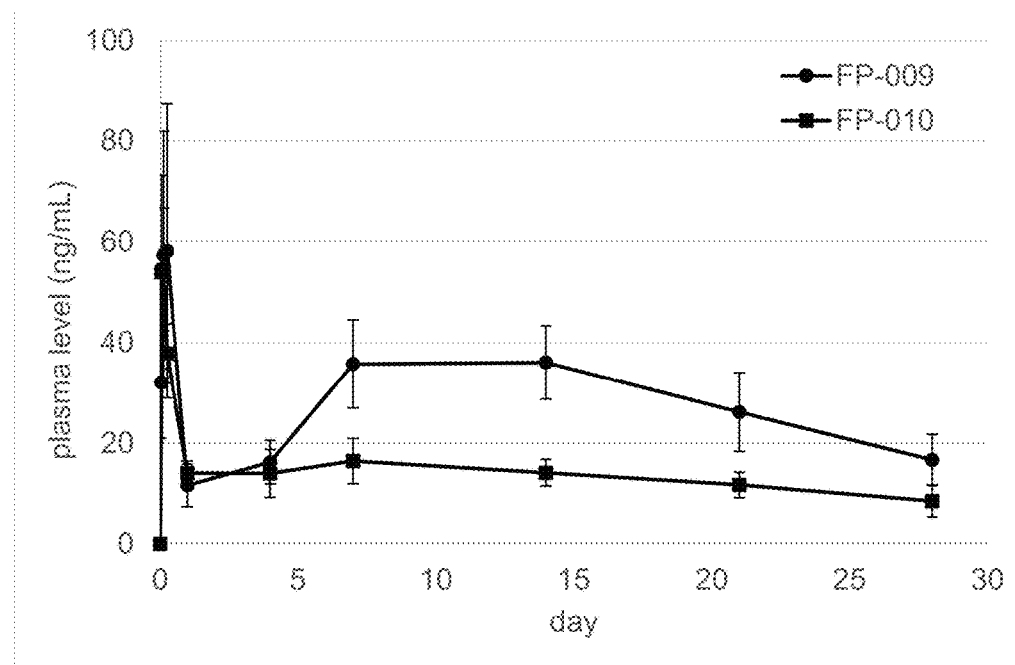
Figure 3 PK profile of Bup/OA/BA formulation v.s. Bup/PLGA/NMP formulation administrated subcutaneously at the dose level of 75 mg/kg (N=6). Standard deviations were labeled as error bars.
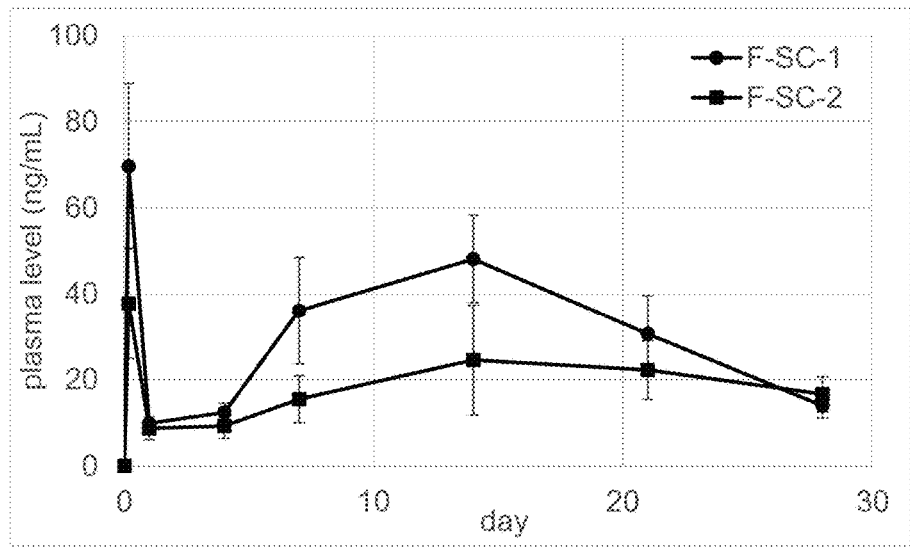
Figure 4. PK profiles of F-SC-1 (5% OA) and F-SC-2 (18% OA), administrated subcutaneously with 75mg/kg dose level (N=5). Standard deviations were labeled as error bars.

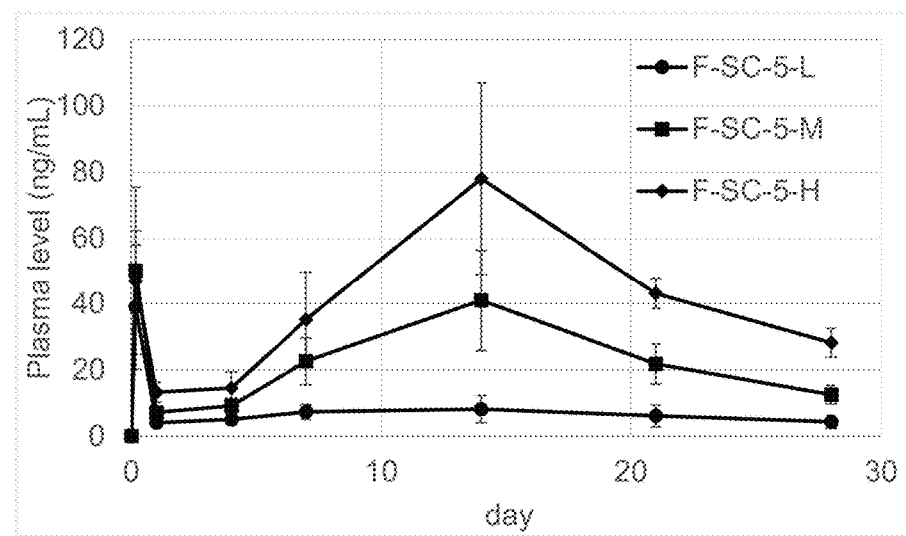
Figure 5. PK profiles of F-SC-5-L, F-SC-5-M and F-SC-5-H, administrated subcutaneously with low (L), medium (M) and high (H) dose level (25, 75, 150mg/kg, N=5), respectively. Standard deviations were labeled as error bars.
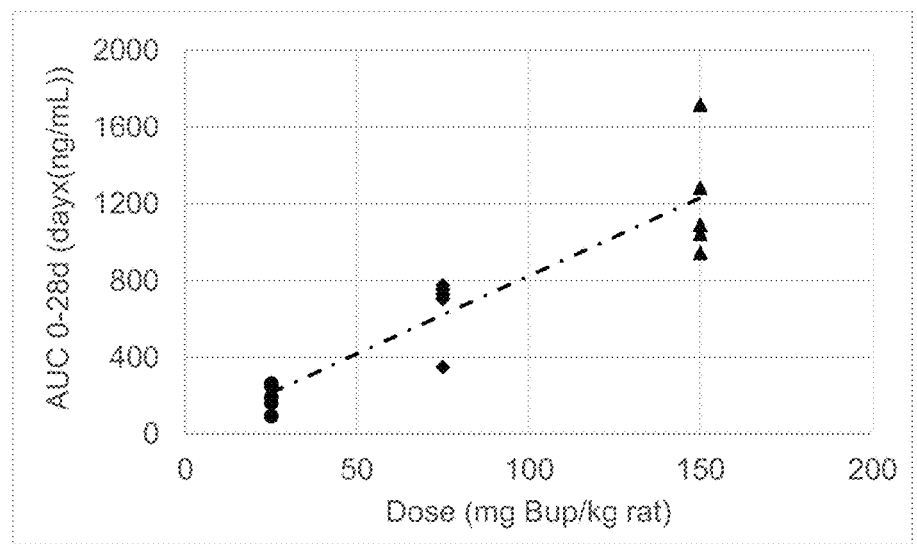
Figure 6. Area under curve with respect to dose levels administrated subcutaneously with F-SC-5.

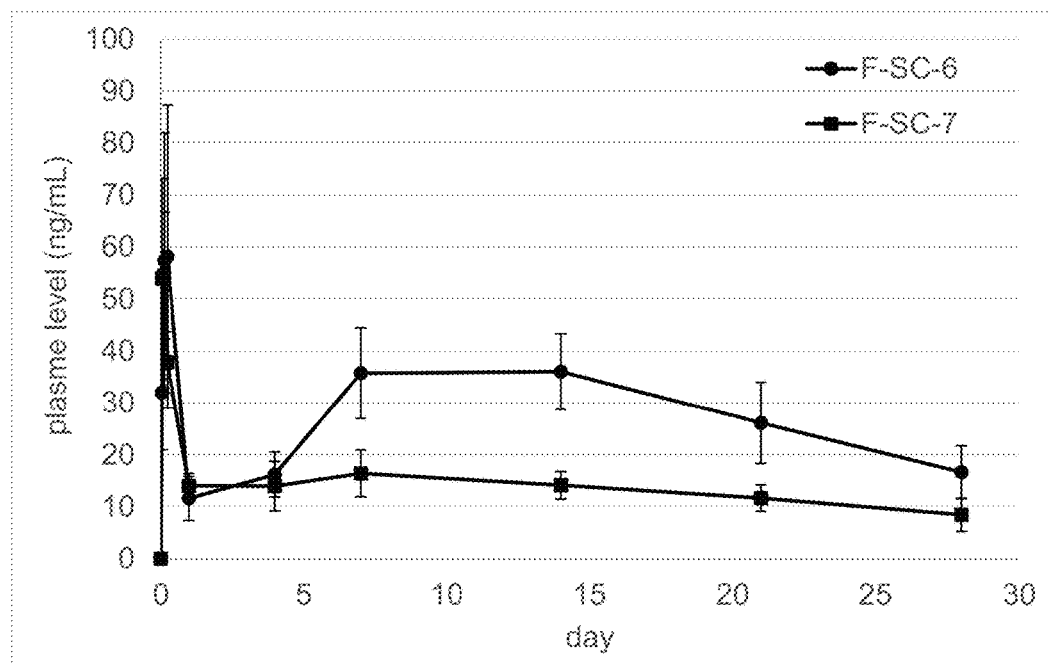
Figure 7 PK profile of Bup/BA/OA formulation vs. Bup/PLGA/NMP formulation. Dose level was 75 mg/kg and N=6. Standard deviations are labeled as error bars.

PHARMACEUTICAL COMPOSITION FOR SUSTAINED RELEASE DELIVERY OF BUPRENORPHINE

FIELD OF THE INVENTION

The field of the invention relates to a delivery system for the sustained and controlled release delivery of buprenorphine. More particularly, the invention relates to a sustained release delivery system that contains a pharmaceutically acceptable organic solution of buprenorphine, a metabolite, a prodrug, or their salts thereof. In addition, the suitable antioxidant alone or combination is included to provide both physical and chemical stabilities.

BACKGROUND OF THE INVENTION

Opioid dependence is a serious medical condition of opioid addiction and is characterized by a compulsive use of opioids (e.g., morphine, heroin, codeine, oxycodone, hydrocodone, etc.). Opioid dependence resulted in 51,000 deaths in 2013 up from 18,000 deaths in 1990 (GBD 2013 *Mortality and Causes of Death, Collaborators* (17 Dec. 2014). "*Global, regional, and national age-sex specific all-cause and cause-specific mortality for* 240 *causes of death,* 1990-2013: *a systematic analysis for the Global Burden of Disease Study* 2013". Lancet 385: 117-171). The societal impact of opioid dependence is substantial in terms of costs related to health care, mental illness, quality of life, lost work productivity, criminal activity, and social welfare expenditure (Hall W, Doran C, Degenhardt L, Shepard D. *Illicit opiate abuse.* In: Jamison D T, Breman J G, Measham A R, et al, eds. *Disease Control Priorities in Developing Countries.* 2nd ed. Washington (DC): World Bank; 2006. Chapter 48). Illicit opioid use posts serious potential risks include the transmission of the human immunodeficiency virus (HIV), hepatitis B virus, hepatitis C virus (HCV), and tuberculosis, as well as a high incidence of death due to respiratory depression and overdose. It is well recognized that the abuse of prescription opioids is on the rise in North America. US medical emergencies related to opioid misuse increased by 183% between 2004 and 2011 (*Trends in U.S. Emergency Department Visits for Opioid Overdose,* 1993-2010, Hasegawa, et al, *Pain Medicine,* Volume 15, Issue 10, 1 Oct. 2014, Pages 1765-1770). Clearly, it would be highly desirable to have therapies that are safe, effective and easy to comply with.

Buprenorphine (also known as (2S)-2-[(−)-(5R,6R,7R,14S)-9a-cyclo-propyl-methyl-4,5-epoxy-6,14-ethano-3-hydroxy-6-methoxymorphinan-7-yl]-3,3-di-methylbutan-2-ol having the chemical structure as shown in formula below.

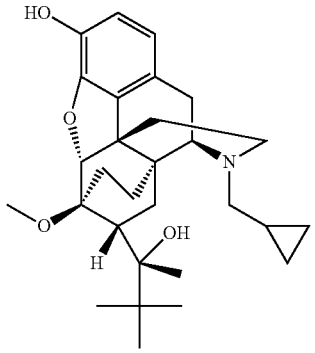 [SMILES: CO[C@]12CC[C@@]3(C[C@@H]1[C@](C)(O)C(C)(C)C)[C@H]1Cc4ccc(O)c5c4[C@@]3(CCN1CC1CC1)[C@H]2O5]

Buprenorphine is a partial μ-opiate receptor agonist and μ-antagonist. It is a potent analgesic with a relatively long duration of action and also possesses an interesting and unique mixed partial μ-agonist-antagonist profile, which makes it useful therapeutically for detoxification and maintenance treatment of opioid-dependent patients. Sublingual tablet/film formulations containing buprenorphine (Subutex® and Suboxone®), Bunavail™, and Zubsolv™ are currently approved in the U.S. for the treatment of opioid dependence. All books, articles and patents referenced herein are fully incorporated by references.

These products can only deliver therapeutic levels of buprenorphine up to several hours. Patients are required to take these medications at regular intervals multiple times daily. However, the compliance is typically an issue with opioid dependent patients and there often are problems with diversion. Therefore, a sustained, controlled delivery of buprenorphine to achieve relative constant and effective dose in patients over a long period of time would be highly desirable to improve patient compliance and treatment outcome.

Various sustained release systems such as solid implants, microparticles, injectable flowable polymeric formulations have been used in delivering pharmaceuticals for an extended period. However, solid implants typically require surgical implantation and furthermore, for the nondegradable delivery systems, a second surgical procedure is required to remove the empty reservoir such as in the case of Probuphine®. Manufacturing process of microparticles is quite complicated and on the other hand, the biodegradable polymer liquid formulations such as Atrigel often have stability issues, which result in the packaging of carrier and active in different containers such as in the case of Eligard®.

Another method employed to extend the delivery of buprenorphine is to synthesize buprenorphine prodrugs by esterifying a drug to form a bio-convertible ester bond and then formulating it in an injectable oily formulation that forms a drug reservoir at the site of injection. (Liu K S and et al. *Anesth Analg.* 2006 May; 102(5):1445-51. US Patent Application: 2005/0075361 and U.S. Pat. No. 7,084,150). Although an effective duration up to 5 days was achieved, covalent esterification may change the characteristics of buprenorphine and may result in unexpected/unwanted toxicities. In addition, prodrugs are typically reviewed as new chemical entity and require significantly more in vitro and in vivo preclinical testing and human clinical trials.

More recently, a subcutaneously sustained release buprenorphine delivery developed by Indivior was approved by the US FDA under trade name of Sublocade™ in late of 2017. Sublocade™ is the first once-monthly injectable buprenorphine formulation for the treatment of moderate to severe opioid use disorder (OUD) in patients who have initiated treatment with a transmucosal buprenorphine-containing product followed by dose adjustment for a minimum of seven days. Sublocade™ is based on biodegradable Atrigel polymer delivery technology. The Atrigel polymer delivery technology includes a poly (DL-lactide-co-glycolide) (PLGA) or poly (DL-lactide) (PLA) with N-methly pyrrolidone (NMP) (U.S. Pat. No. 8,775,270, US Patent Application 2016/0128997 A1). The major components in Sublocade™ include a poly (DL-lactide-co-glycolide) (PLGA) with N-methly pyrrolidone (NMP) and the active ingredient, buprenorphine (U.S. Pat. No. 8,921,387). Even though Sublocade™ prepared by dissolving buprenorphine in Atrigel system can be filled in a prefilled syringe without mixing step before usage, there are still other drawbacks, for example due to high viscosity of formulation, a large needle (19 gauge) for the injection could cause discomfort in patient and decrease the compliance. Besides, the color change over time (from colorless initially to amber) could be another indicator for the stability issue. In addition, the recommended dose of Sublocade™ following induction and dose adjustment with transmuscosal buprenorphine is 300 mg monthly for the first two months followed by a maintenance dose of 100 mg monthly. The leading dose of Sublocade™ is 300 mg, equivalent 1.5 mL injection volume. This large amount of dosage will then solidify in subcutaneous tissue to form a depot. It is known PLGA depot swells by absorbing tissue liquid, thus aggravating the discomfort to medication receivers (Sequeira J. A. D., et al., *Poly(lactic-co-glycolic acid) (PLGA) matrix implants*. Chapter 10 Nanostructures for the Engineering of Cells, Tissues and Organs, 2018, Pages 375-402). Therefore, there is a need for further improvement.

Another subcutaneously administered sustained release buprenorphine dosage was approved by the EMA/FDA under trade name of Buvidal®/Brixadi™ in late 2018. There are weekly and monthly dosage of Buvidal® treating moderate to severe opioid use disorder (OUD). Buvidal® encapsulates buprenorphine by a lipid-based matrix with a tradename as FluidCrystal®. The major components in Buvidal® include a phospholid, as phosphatidyl choline, diacyl ester, as glycerol dioleate, solvent, as ethanol or NMP, and the active ingredient, buprenorphine (U.S. Pat. Nos. 8,236,755 and 9,937,164). FluidCrystal® also forms solid depot after injection, in which phosphatidyl choline would gradually lyse adipose tissue and may aggravate the discomfort (Rotunda, A. M., Kolodney, M. S. *Mesotherapy and Phosphatidylcholine Injections: Historical Clarification and Review. Dermatologic Surgery*, (2006) 32(4), 465-480). Moreover, though the volume of single injection (0.64 mL) contributed by Buvidal® seems smaller than the volume of Sublocade™ (1.5 mL), the cumulative injected volume in a month of Buvidal® can be as large as 2.6 mL. Thus, the discomfort may be not less than discomfort caused by Sublocade injection.

Both commercial subcutaneous injection buprenorphine product, including Sublocade™ and Buvidal® are not color stable. Both changes color over time, from colorless to amber (*FDA advisory committee meeting briefing document: Indivior RBP*-6000: pp 30 Oct. 31, 2017 and *Braeburn Pharmaceutical CAM* 2038 pp 29 Nov. 1, 2017). Not only for the aesthetic issue, this discoloration would increase the challenge of chemistry, manufacturing and control (CMC) because color is always a key attribute in specification of parenteral pharmaceuticals. Additionally, based on label information, both products are granted with 18-month shelf-life, which is not ideal from an aspect of small-molecule drug products.

For a parenteral injection product, especially for a solution-based formulation, the stabilities (both physical and chemical) and injectability are the key parameters during the development. The minimum change of physical and chemical properties over time are required to have a suitable period of time for shelf storage. In addition, the injectability via smaller gauge needle, such as less than 23 gauge needle, can improve the comfort of patient and further enhance the patient compliance.

Though two commercial products have existed, there is still need to develop better injectable sustained-release buprenorphine dosage. Particularly, improvement on the depot size, stabilizing the color deterioration, prolonging the shelf-life, enhancing drug release/absorption, and mitigating the pain of injection are still highly desirable.

SUMMARY OF THE INVENTION

The present invention provides a stabilized buprenorphine sustained release pharmaceutical composition capable of delivering buprenorphine, a metabolite, a prodrug or their salts thereof over an extended period of time. The pharmaceutical composition possesses enhanced ability to maintain appropriate properties, such as color change, injectability, and chemical stability. The composition can deliver a therapeutically effective level of buprenorphine for at least 7 days, preferably at least about 28 days, or up to at least 3 months to treat patients for opioid dependence, pain or other indications.

Buprenorphine sustained release delivery can be achieved by the composition comprising A) buprenorphine or its salt or metabolite or prodrug up to 50% by weight, and B) a pharmaceutically acceptable organic solvent.

The pharmaceutically acceptable organic solvent is selected from the group comprising of ethanol, benzyl alcohol (BA), benzyl benzoate (BB), propylene glycol (PG), glycol, N-methyl pyrrolidone (NMP), glycofurol, dimethylacetamide (DMAc), dimethylsulfoxide (DMSO), polyethylene glycol 300 (PEG300), and polyethylene glycol 400 (PEG400), and a combination of two or more thereof. The especially preferred pharmaceutically acceptable solvent is benzyl alcohol.

The content of the pharmaceutically acceptable solvent in the pharmaceutical composition is from 5% to 90% by weight.

The pharmaceutical composition of the present invention further comprises a suitable antioxidant.

The stabilized buprenorphine sustained release delivery can also be achieved by the composition comprising A) buprenorphine or its salt or metabolite or prodrug up to 50% by weight, B) pharmaceutically acceptable organic solvent, C) fatty acid and D) suitable antioxidants. The fatty acid can be selected from the group of saturated or unsaturated fatty acid with various carbon chain length. The incorporation of fatty acid can be served as a synergistic co-solvent with pharmaceutically acceptable organic solvent enhancing the solubility of buprenorphine. Formulation with higher solubility can decrease the overall needed injection volume to improve the patient comfort and compliance. Fatty acid has additional benefits such as improved bioavailability.

The saturated fatty acid can be selected from the group of $C_8$-$C_{20}$ fatty acid, for example, caprylic acid, capric acid, undecylic acid, lauric acid, tridecylic acid, myristic acid, pentadecylic acid, palmitic acid, margaric acid, stearic acid, nonadecylic acid and arachidic acid. The unsaturated fatty acid can contain more than one unsaturated bond with $C_8$-$C_{20}$ carbon length, for example, palmitoleic acid, vaccenic acid, paullinic acid, oleic acid, elaidic acid, linoleic acid, linoleldidic acid, γ-linolenic acid, α-linolenic acid, and stearidonic acid. The especially preferred fatty acid is oleic acid (OA).

The content of the fatty acid in the pharmaceutical composition is from 0.1% to 50% by weight, preferably from 1% to 15% by weight.

The pharmaceutical composition further comprised antioxidant alone or in combination. The antioxidants can be selected from the group consisting of butylated hydroxyanisole (BHA), butylated hydroxytolene (BHT), tocopherol, ascorbic acid (VC), ascorbyl palmitate, citric acid, propyl gallate, L-methionine (Met), monothioglycerol (MTG), sodium glycolate (STG), Lipoic acid (LipA), thioglycolic acid (TGA), sodium metabisulfite, monoethanolamine gentisate, L-cysteine (Cys), N-acetyl L-cysteine, cysteamine (CysA) reduced-glutathione (Glu), and sodium EDTA.

The pharmaceutical composition of the present invention does not include polymeric controlled-release material such as PLA and PLGA.

The pharmaceutical composition of the present invention has a narrow fluctuation of buprenorphine plasma level or the peak-to-trough ratio is less than 20, preferably less than 10, and more preferably less than 5.

Surprisingly, among these common antioxidants, some of the thiolated antioxidants, such as MTG, STG, and TGA, selectively presented stronger capacity of color mitigation in buprenorphine formulation overtime under stress condition, while other antioxidants (Glu, Cys and LipA) displayed milder color stabilizing effect.

Even though the color mitigation in buprenorphine formulation can be successfully achieved with addition of thiolated antioxidant, such as MTG, the benzaldehyde (BZ), oxidation of benzyl alcohol, produced significantly after same period of incubation condition unexpectedly.

Without bound to the theory, the oxidation of benzyl alcohol might be formed via metal-catalyzed oxidation mechanism or disulfide oxidation-reduction reaction or radical oxidation mechanism. However, with presence of metal chelator, EDTA or reducing agent, TCEP (tris(2-carboxyethyl)phosphine), benzyl aldehyde was still formed and increased with time.

Surprisingly and unexpectedly, with selective addition of VC, the production of benzaldehyde can be significantly reduced with addition of MTG. With other chemical stabilizers, such as sodium EDTA (chelating agent) and TCEP (disulfide reducing agent), benzyl aldehyde formation still occurs in the presence of MTG.

Even though the thiolated reagent can be also used as radical scavenging agent, such as 2-mecapoethanol, the MTG in the formulation indeed promotes the benzyl aldehyde formation. The actual mechanism is still unknown. Not all of the thiolated antioxidant or reagent promoted the benzyl aldehyde formation. For example, the MTG, STG, Cys and CysA revealed the positive benzyl aldehyde formation, but the Glu showed the opposite effect on benzyl aldehyde formation. Interestingly and unexpectedly, with addition of VC, only the STG and MTG containing BA/OA solution revealed the inhibition effect of benzyl aldehyde, the rest of the thiolated containing BA/OA solution did not show the benzyl aldehyde mitigation with VC.

The concentration of MTG is in the range of 0.01% to 2% by weight. The concentration of MTG is preferably at least 0.1% by weight, or more preferably at least 0.3% by weight or the most preferably at least 0.5% by weight.

The concentration of VC may be in the range of 0.01% to 1% by weight. The concentration of VC is preferably at least 0.01% by weight or the more preferably at least 0.02% by weight or the most preferably at least 0.05% by weight.

The effective ratio of MTG/VC is selected in the range of 1 to 50, preferably in the range of 5 to 40, or more preferably in the range of 10 to 30.

Pharmaceutical composition can be injected through a small gauge needle, preferably through 21 gauge needle, or more preferably through 23 gauge needle or most preferably through 25 gauge needle or smaller diameter needle.

The pharmaceutical composition can have the viscosity no more than 1000 Centipoise (cPs), more preferably less than 100 cPs, and most preferably less than 25 cPs to improve the injectability.

The pharmaceutical composition may be pre-filled into one syringe to form a product in a ready-to-use configuration.

BRIEF DESCRIPTION OF THE DRAWINGS

FIG. 1. Shows the effect of antioxidant mitigating discoloration in buprenorphine formulation. Tested formulation was stored at 60° C. for 14 days.

FIG. 2 Shows PK profiles in rats (N=5) of subcutaneously-administrated buprenorphine formulations, FP-006 to FP-008.

FIG. 3 PK profile in rats (N=6) of Bup/OA/BA formulation (FP-009) v.s. Bup/PLGA/NMP (FP-010) formulation.

FIG. 4 Shows PK profiles in rats (N=5) of F-SC-1 (5% OA) and F-SC-2 (18% OA), administrated subcutaneously with 75 mg/kg dose level.

FIG. 5 Shows PK profiles in rats (N=5) of F-SC-5-L, F-SC-5-M and F-SC-5-H, administrated subcutaneously with low (L), medium (M) and high (H) dose level (25, 75, 150 mg/kg, N=5), respectively.

FIG. 6 Shows the correlation of Area under curve with respect to dose levels administrated subcutaneously with F-SC-5.

FIG. 7 shows PK profile of Bup/BA/OA formulation vs. Bup/PLGA/NMP formulation. Dose level was 75 mg/kg and N=6. Standard deviations are labeled as error bars.

DETAILED DESCRIPTION OF THE INVENTION

The present invention is directed to a sustained release delivery system for buprenorphine. As used herein, the singular forms "a," "an," and "the" include plural reference unless the context clearly dictates otherwise. Thus, for example, a reference to "a formulation" includes a plurality of such formulations, so that a formulation of buprenorphine includes formulations of buprenorphine.

As used herein, the term "pharmaceutically acceptable" means that the material, substance, compound, molecule, polymer, or system to which it applies should not cause severe toxicity, severe adverse biological reaction, or lethality in an animal to which it is administered at reasonable doses and rates.

As used herein, the term "pharmaceutically acceptable salts" refer to derivatives wherein the parent compound is modified by making acid or base salts thereof. Suitable acceptable salts include, but are not limited to, mineral or organic acid salts of basic residues such as amines; alkali or organic salts of acidic residues such as carboxylic acids; and the like. The acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methane-sulfonic, ethane disulfonic, oxalic, isethionic, and the like. Specifically, the acceptable salts can include, for example, those salts that naturally occur in vivo in a mammal.

As used herein, the term "therapeutically effective amount" is intended to include an amount of buprenorphine, a pharmaceutically acceptable salt thereof, useful to treat or prevent the underlying disorder or disease, or to treat the symptoms associated with the underlying disorder or disease in a host.

As used herein, "synergistic effect" is an effect arising between two or more agents, entities, factors, or substances that produces an effect greater than the sum of their individual effects.

The present invention provides a stabilized buprenorphine sustained release delivery pharmaceutical composition capable of delivering buprenorphine, a metabolite, a prodrug or their salts thereof over an extended period of time. The term "stabilized", in one aspect, as used herein denotes to a status to remain substantially unchanged pharmaceutical compositions under a specified storage condition, during the period between the time it is prepared and the time to be re-tested. Particularly, the invention provides a method of enhancing stability of the composition of the present application so that the composition does not vary more than 10%, more than 5%, more than 3%, or 2% over a period of one week, one months, three months, six months or longer under specified storage conditions. The storage conditions may include regular temperature or elevated temperature, including 30° C., 40° C., 50° C., 60° C. or above.

In a further aspect, the invention provides a method of enhancing color stability of the composition of the present application so that the apparent color of buprenorphine composition retains as colorless to pale yellow (comparable USP color standard A to E, described in USP <631>). The term "extended period" as used herein denotes a period over one week, one month, three months, six months or longer under specified storage conditions. The storage conditions may include regular temperature or elevated temperature, including 30° C., 40° C., 50° C., 60° C. or above.

The present invention relates to a pharmaceutical composition comprising 1) at least 1 wt % of buprenorphine or its salt thereof; 2) a pharmaceutically acceptable solvent selected from the group consisting of ethanol, benzyl alcohol (BA), benzyl benzoate (BB), propylene glycol (PG), glycol, glycofurol, polyethylene glycol 300 (PEG300), and polyethylene glycol 400 (PEG400), and a combination of two or more thereof.

In one aspect, the buprenorphine in the pharmaceutical composition is in the form of the free base. The buprenorphine in the pharmaceutical composition is present in an amount of 1 wt % to 40 wt %, preferably of 5 wt % to 35 wt %, more preferably of 10 wt % to 30 wt %.

In another aspect, the pharmaceutically acceptable solvent in the pharmaceutical composition is benzyl alcohol (BA).

In another aspect, the pharmaceutically acceptable solvent in the pharmaceutical composition is glycofurol.

In another aspect, the pharmaceutically acceptable solvent in the pharmaceutical composition is polyethylene glycol.

In another aspect, the pharmaceutical composition of the present invention does not need to use PLA or PLGA to achieve sustained release delivery of buprenorphine. This makes the preparation of formulations much easier and allow the use of a simpler formulation to achieve the same therapeutic outcome.

The present invention further provides a pharmaceutical composition comprising 1) at least 1 wt % of buprenorphine or its salt thereof; 2) a pharmaceutically acceptable solvent selected from the group consisting of ethanol, benzyl alcohol (BA), benzyl benzoate (BB), propylene glycol (PG), glycol, N-methyl pyrrolidone (NMP), glycofurol, dimethylacetamide (DMAc), dimethylsulfoxide (DMSO), polyethylene glycol 300 (PEG300), and polyethylene glycol 400 (PEG400), and a combination of two or more thereof; and 3) a fatty acid.

In one aspect, the buprenorphine in the pharmaceutical composition is in the form of the free base. The buprenorphine in the pharmaceutical composition is present in an amount of 1 wt % to 40 wt %, preferably of 5 wt % to 35 wt %, more preferably of 10 wt % to 30 wt %.

In another aspect, the pharmaceutically acceptable solvent in the pharmaceutical composition is benzyl alcohol (BA).

In another aspect, the fatty acid in the pharmaceutical composition is selected from the group consisting of caprylic acid, capric acid, undecylic acid, lauric acid, tridecylic acid, myristic acid, pentadecylic acid, palmitic acid, margaric acid, stearic acid, nonadecylic acid, arachidic acid, palmitoleic acid, vaccenic acid, paullinic acid, oleic acid, elaidic acid, linoleic acid, linoleldidic acid, γ-linolenic acid, α-linolenic acid, and stearidonic acid. The fatty acid is present in an amount of either 0.1 wt % to 40 wt %, or 1 wt % to 30 wt % or 3 wt % to 10 wt %.

In another aspect, the fatty acid in the pharmaceutical composition is oleic acid.

The present invention further provides a pharmaceutical composition comprising 1) at least 1 wt % of buprenorphine or its salt thereof; 2) a pharmaceutically acceptable solvent selected from the group consisting of ethanol, benzyl alcohol (BA), benzyl benzoate (BB), propylene glycol (PG), glycol, N-methyl pyrrolidone (NMP), glycofurol, dimethylacetamide (DMAc), dimethylsulfoxide (DMSO), polyethylene glycol 300 (PEG300), and polyethylene glycol 400 (PEG400), and a combination of two or more thereof; 3) a fatty acid; and 4) a stabilizer. Wherein the buprenorphine serves as the bioactive agent, which is known for its therapeutic effect in opioid use disorder (OUD) and pain management; fatty acid serves as both a solubility enhancer and a bio-absorption enhancer; organic solvent serves as a dissolving agent and also a carrier; stabilizing agents suppress the chemical degradation of components in formulations provided herein.

In one aspect, the buprenorphine in the pharmaceutical composition is in the form of the free base. The buprenorphine in the pharmaceutical composition is present in an amount of 1 wt % to 40 wt %, preferably of 5 wt % to 35 wt %, more preferably of 10 wt % to 30 wt %.

In another aspect, the pharmaceutically acceptable solvent in the pharmaceutical composition is benzyl alcohol (BA).

In another aspect, the fatty acid in the pharmaceutical composition is selected from the group consisting of caprylic acid, capric acid, undecylic acid, lauric acid, tridecylic acid, myristic acid, pentadecylic acid, palmitic acid, margaric acid, stearic acid, nonadecylic acid, arachidic acid, palmitoleic acid, vaccenic acid, paullinic acid, oleic acid, elaidic acid, linoleic acid, linoleldidic acid, γ-linolenic acid, α-linolenic acid, and stearidonic acid. The fatty acid is present in an amount of either 0.1 wt % to 40 wt %, or 1 wt % to 30 wt % or 3 wt % to 10 wt %.

In another aspect, the fatty acid in the pharmaceutical composition is oleic acid.

In another aspect, the stabilizer in the pharmaceutical composition is selected from a group comprising of L-methionine (Met), monothioglycerol (MTG), glutathione (Glu) and lipoic acid (LipA), ascorbic acid (VC) and ethylenediaminetetraacetic acid (EDTA). Monothioglycerol (MTG) and ascorbic acid (VC) are preferred stabilizers. They can be used alone or in combination. When the combination of monothioglycerol (MTG) and ascorbic acid (VC) is used, a ratio of MTG/VC from 1 to 100 is desired.

In another aspect, the monothioglycerol (MTG) and ascorbic acid (VC) in the pharmaceutical composition are from 0.1% to 2.0% and 0.01% to 0.05%, respectively.

In another aspect, the color of pharmaceutical composition will remain colorless to pale yellow after stored at 60° C. for 3 months.

In all aspects described above, the present invention relates to a substantially concentrated buprenorphine formulation as a flowable liquid for an extended period of time. The "extended period of time" as used herein denotes a period over one week, one month, three months, six months or longer under specified storage conditions. The storage conditions may include room temperature or elevated temperature, including 30° C., 40° C., 50° C., 60° C. or above. The term "substantially concentrated" as used herein means the composition described herein comprises at least 5% of buprenorphine base, metabolites or salts by weight (wt %), preferably at least 15 to wt % buprenorphine, and more preferably at least 25 wt % buprenorphine. In one aspect, the term "flowable liquid" as used herein means the composition is clear and non-viscous solution, characterized without any visible particulates or opaque emulsion.

In one aspect, due to low viscosity, the buprenorphine composition of the present invention can readily to be transported using regular pump as peristaltic, rotary or piston pump, and to then fill into suitable containers including vials, ampules and prefillable syringes. The appropriate material for container includes type I (borosilicate) glass and highly chemical-resistant plastic, including cyclic olefin copolymer (COC), cyclic olefin polymer (COP) and polypropylene (PP). The suitable sealing material of stopper and plunger are butyl rubber laminated with chemical-resistant fluoropolymer, such as polytetrafluoroethylene (PTFE or Teflon®) and polythylenetetrafluoroethylene (ETFE or Furotec®).

In a further aspect, the present invention provides a high concentration and non-viscous solution of buprenorphine which can be easily injected using small size needles. The buprenorphine solution provided in the present invention in a 1 mL syringe can be injected through a small size of needle manually or using injectors with a force less than 30 Newtons (N), preferably less than 10 N. The suitable size of needle may be 23 gauge to 30 gauge with a length of 8 to 25-mm. The preferred size of needle is 25 to 30 gauge, preferably 27 to 30 gauge. The present invention provides an injection with potentially less pain due to the use of smaller size needles. This is different from the existing products such as polymeric or oil depot that often requires needles larger than size of 19 gauge.

The present invention provides a method using fatty acid as a solubility enhancer of buprenorphine composition. The term "solubility" as used herein denotes a saturated concentration of a solid solute in a concomitant liquid solvent. Without further remark, the saturated concentration was evaluated at room temperature. The term "enhancer" as used herein means with the addition of the component in solvent, the saturated concentration in the two-component system is higher than the saturated concentration in single-component solvent. The strength of solubility enhancement provided by fatty acid is at least 10%, or at least 30%, or at least 50%. The suitable fatty acid can be either saturated or unsaturated fatty acid. Examples of saturated fatty acid comprises the group of $C_8$-$C_{20}$ carbon chain, including caprylic acid, capric acid, undecylic acid, lauric acid, tridecylic acid, myristic acid, pentadecylic acid, palmitic acid, margaric acid, stearic acid, nonadecylic acid and arachidic acid. The unsaturated fatty acid may present one or more than one unsaturated bonds in the chain of $C_{10}$-$C_{20}$ carbon length, including palmitoleic acid, vaccenic acid, paullinic acid, oleic acid, elaidic acid, linoleic acid, linoleldidic acid, γ-linolenic acid, α-linolenic acid, and stearidonic acid. The preferable fatty acid is oleic acid. The suitable content of fatty acid in buprenorphine solution presented in this invention will be from 0.1 to 50 wt %.

In another aspect, the appropriate addition of organic solvent significantly reduces viscosity of highly concentrated buprenorphine formulation, thus improving the injectability and reducing the force during injection, including breakthrough and gliding force. Suitable examples of biocompatible organic solvent include but is not limited to common pharmaceutically acceptable solvents as ethanol, benzyl alcohol, benzyl benzoate, N-methyl pyrrolidone (NMP), dimethylacetamide (DMAc), dimethylsulfoxide (DMSO), polyethylene glycol (PEG) 200 to 600, triethylene glycol, propylene glycol (PG), glycofural, triacetin and glycerol. The preferred biocompatible organic solvent is benzyl alcohol. In all aspects of the invention, the content of the biocompatible organic solvent in buprenorphine solution will range from 10 to 90 wt %. The preferable proportion of organic solvent ranges from 30 to 80 wt %.

In an unexpected aspect, the invention provides a combination of fatty acids and organic solvents. The solubility of buprenorphine is higher in the combination of the two than that in either organic solvent alone or fatty acid alone. The synergistic effect of enhancing the solubility of buprenorphine is surprising and unexpected. Without being bound by theory, the multiple-component enhancement could be established by two potential liquid-state principles individually or in parallel. First, fatty acids may attach to highly hydrophobic buprenorphine molecule by the aliphatic chain and allow the carboxylic group exposed to polar solvent, thus interfacing the polar interaction between buprenorphine and solvent, thus enhancing the solvation of buprenorphine molecules and the corresponding higher solubility. Second, the potential negatively charged carboxylic group on fatty acid could interact with potential positively charged amine group on buprenorphine molecule. This electronic ion pair may form quasi ionic bond between fatty acid and buprenorphine, thus increasing the polar interaction between buprenorphine and solvent and enhancing the solvation of buprenorphine molecules. The fatty acid-organic solvent mixture that capable of multiple-component solubility enhancement in the present invention may possess a ratio of solvent to fatty acid ranging from 100:1 to 1:1 (wt/wt). Comparing to buprenorphine solubility in organic solvent or fatty acid, the multiple-component buprenorphine solubility enhancement results in at least 2 wt % solubility enhancement. The preferred multiple-component buprenorphine solubility enhancement is at least 5 wt % and more preferred multiple-component buprenorphine solubility enhancement is at least 8 wt %. The preferred solvents and fatty acids are benzyl alcohol and oleic acid, respectively.

The present invention particularly provides a method using color stabilizing agent to maintain the color stability of buprenorphine composition. Surprisingly, the color stabilizing capacity is not universally possessed by commonly used pharmaceutical antioxidants, such as ascorbic acid (VC) (Example 1), in which the color of buprenorphine composition was darken to color freely discernable by visual inspection, which may lead to the failure in quality control and assurance. The color deterioration in buprenorphine formulation clearly differs from the observation in prior experience of buprenorphine formulation as in U.S. Pat. No. 6,365,596, in which the discoloration in buprenorphine-comprised product can be mitigated by the presence of ascorbic acid with 1 to 3 equivalence of buprenorphine.

It was found that the thiolated antioxidant is able to stabilize the color of buprenorphine composition of the present invention. The suitable color stabilizing agent is thiolated antioxidants including monothioglycerol (MTG) and thioglycolic acid (TGA), preferably MTG. The suitable content of thiolated antioxidant ranges from 0.05 to 2 wt %, preferably 0.1 to 1 wt %.

It was unexpectedly found that thiolated antioxidants though displaying effective color stabilizing ability, may not improve the chemical degradation of buprenorphine, from the aspect of purity or total impurity content. This discovery is different from the function of thiolate-based protection described in U.S. Pat. No. 9,668,967 in which it is disclosed that thiolated antioxidant effectively mitigates both chemical degradation and discoloration in buprenorphine solution. Thus, the fact that thiolated antioxidant worked differently in buprenorphine formulation in prior art and buprenorphine composition provided in the present invention suggest a possibility the chemical degradation related to total impurity in the buprenorphine composition provided in the invention may be also different from degradation mechanism disclosed in U.S. Pat. No. 9,668,967. The distinguishable degradative pathway in composition in the present invention may be specific and subjected to fatty acid and organic solvent.

In another aspect, thiolated antioxidant as MTG or TGA is found to stimulate the degradation of inactive ingredient in the composition provided in the invention. The degradation is mostly found in organic solvent in composition, particularly found in the presence of benzyl alcohol (BA). With presence of BA and MTG or TGA and without other antioxidant, the content of benzaldehyde (BZ), oxidized from benzyl alcohol in the composition increases over time during storage. This degradation of benzyl alcohol found is significantly lower in buprenorphine composition with absence of thiolated antioxidants. Quantitatively, the thiolated antioxidant stimulates the generation of benzaldehyde by 1, 2 or 3-fold.

In another aspect, the thiolated antioxidant-induced degradation of benzyl alcohol cannot be reduced by the treatment of nitrogen purging for de-oxygenating the combination of benzyl alcohol and fatty acid vehicle. It is said that the generation of benzaldehyde is oxygen independent. In an antioxidant selection table in a review paper (Waterman K C et al., *Stabilization of Pharmaceuticals to Oxidative Degradation Pharmaceutical Development and Technology*, (2002) 7(1), 1-32)), there is no recommended antioxidants for non-aqueous liquid dosage for mitigating oxygen independent oxidative degradation, further indicating the rare incidence of the thiolated antioxidant-induced oxygen-independent oxidation of benzyl alcohol. In contrast, the degradation of buprenorphine can be significantly reduced by the treatment of nitrogen purging to combination of benzyl alcohol and fatty acid vehicle for an extended period of time under specified storage condition. The term "extended period" as used herein denotes a period over one week, one month, three months, six months or longer under specified storage conditions. The storage conditions may include room temperature or elevated temperature, including 30° C., 40° C., 50° C., 60° C. or above.

The severity of benzyl alcohol degradation can be quantitated by the generation of benzaldehyde (BZ). In this aspect, the invention provides a method to quantitatively evaluate the generation of BZ, by the percentage of the peak of BZ in chromatograms using UPLC method described in example section with respect to the total peak area in the corresponding chromatogram, excluding the peak area of vehicle. With presence of some thiolated antioxidants such as MTG or TGA, the BZ area % is at least 1%, 2%, 3%, 5% or 10%, during an extended period of time under specified storage condition.

In one aspect, the present invention provides a method to use the combination of stabilizers to maintain the stability of buprenorphine composition. The term "combination of stabilizers" as used herein related to a composition of antioxidants comprising one thiolated antioxidant and one sulfur-free antioxidant. The examples of antioxidants include ascorbic acid (vitamin C or VC), ascorbyl palmitate, butylated hydroxyanisole (BHA), butylated hydroxytoluene (BHT), propyl gallate and tocopherols (Vitamin E). The suitable content of sulfur-free antioxidant is 0.005 to 0.5 wt %, preferably 0.01 to 0.1 wt %. The suitable content of thiolated antioxidant ranges from 0.05 to 2 wt %, preferably 0.1 to 1 wt %. The preferable sulfur-free and thiolated antioxidant is ascorbic acid and MTG, respectively. The term "stability" as used herein denotes 1) the degradation of buprenorphine in composition provided in the invention is less than 10, 5, 3, 2 or 1% as determined UPLC chromatogram peak areas, 2) the color of buprenorphine composition in the invention remains as colorless to pale yellow, and 3) the generation of benzaldehyde is less than 2, 1, 0.5 or 0.2% as determined UPLC chromatogram peak areas, during an extended period of time under specified storage condition. The storage conditions may include room temperature or elevated temperature, including 30° C., 40° C., 50° C., 60° C. or above. In one aspect, the preferable degradation of buprenorphine no more than 3% and the preferable generation of benzaldehyde is no more than 0.5 area %, respectively, during an extended period of time under specified storage condition as previously defined.

In one further aspect, the present invention provides a method to reduce the degradation of buprenorphine in composition using the combination of stabilizers, relative to the compositions without to an extent by at least 30%, preferably by at least 50% and more preferably by at least 70%.

In another aspect, the invention provides a method to reduce the degradation of benzyl alcohol in the composition using the combination of stabilizers, relative to the composition without, to an extent by at least 30%, preferably by at least 50% and more preferably by at least 70%.

Particularly, the present invention provides a method using the combination of stabilizers, comprising VC and MTG, to demonstrate additionally enhanced mitigation of buprenorphine and benzyl alcohol degradation in the buprenorphine composition. Without being bound to theory, this additional enhancement beyond the combination of the effect of stabilization could be contributed by that 1) VC may alleviate the effect of MTG-promoted chemical degradation, 2) MTG may boost the VC-modulated antioxidant protection, or 3) the formerly described effects act simultaneously.

In one aspect, this invention provides a method to sterile buprenorphine composition using a treatment of terminal sterilization. Herein, the buprenorphine composition has been provided in all prior embodiments in this invention. To the author's' knowledge, it has not been disclosed that buprenorphine-organic solvent system can be tolerated with energy-driven terminal sterilization. The term "tolerated" as used herein means the stability will not be decreased by the treatment. The relevant example was provided in U.S. Pat. No. 9,295,645 in which aqueous suspension buprenorphine formulation was claimed to be able to be autoclaved. From the electrochemical aspect, the oxidative potential is lower in aqueous environment than organic solvent. Therefore, it is understandable autoclave method may not lead to significant oxidative degradation to aqueous buprenorphine suspension.

In a further aspect, terminal sterilization method applicable in this invention may include moisture heat autoclave, E-beam, gamma irradiation and UV light. The preferable method is autoclave. The operation parameters of autoclave include: 1) the sterilization temperature is at least 115° C., preferably at least 120° C., and 2) the heating duration with former temperature lasts 10~60 minutes, preferably 20-30 minutes. The suitable containers used in autoclave may include crimped vials, ampules and prefillable syringes, composed of type I glass and thermostable plastic as COP, COC and PP.

In one aspect, the invention provides a method using fatty acid serving as a bio-absorption enhancer of buprenorphine liquid dosage over the duration of sustained release. Herein, the method is applicable while buprenorphine dosage is applied via extravascular administration, preferably via intramuscular and subcutaneous administration and more preferably via subcutaneous administration. Moreover, the term "sustained release" as used herein denotes the delivery of bioactive form a depot, implant or reservoir remaining at a detectable rate over an extended period of time, rather than release immediately to surrounding environment. The duration of sustained release provided by this invention is 1 month, 2 months, 3 months or longer. The suitable content of fatty acid in the buprenorphine dosage is 0.1 to 50 wt %.

In one embodiment, the buprenorphine provided in the invention particularly displays bio-absorption of enhancement during sustained release period, compared to buprenorphine-organic solvent solution. Wherein, the enhancement rate of sustained release by the aid of fatty acid is at least 50% increase of AUC, preferably 70% increase of AUC and the most preferably 100% increase of AUC, over a period of time for 1 month, 2 months, 3 months or longer.

In another aspect, the buprenorphine provided in the invention particularly displays bio-absorption of enhancement during sustained release period, compared to a polymeric buprenorphine dosage. Wherein, the polymeric buprenorphine dosage comprises biodegradable polyester, such as poly (lactic-co-glycolic acid) (PLGA) or polylactic acid (PLA), with molecular weight ranging from 5 to 40 kD. Wherein, the enhancement rate of sustained release by the aid of fatty acid is at least 50% increase of AUC, preferably 70% increase of AUC and the most preferably 100% increase of AUC, over a period of time for 1 month, 2 months, 3 months or longer.

In one further aspect, the invention provides a buprenorphine composition able to deliver sufficient exposure. The term "sufficient exposure" as used herein quantitatively denotes a 28-day dose-normalized postdose area-under-curve (n-$AUC_{0-28d}$) at the level no less than 5 (ng/mL×day)/(mg Bup/kg weight), preferably at the level of no less than 10 (ng/mL×day)/(mg Bup/kg weight). Herein, n-$AUC_{0-28d}$ is extracted by the PK profile in male rats with subcutaneous administration of buprenorphine formulations provided in the invention.

Particularly, the invention provides a method to modulate bio-absorption over sustained release duration. The method relates to a tendency that the AUC inversely increases with Bup/OA ratio (wt/wt). By dosing buprenorphine formulation with Bup/OA ratio at the level of 1, 2, 3, 5, or 10, the dose-normalized AUC may be at the level of no less than 20, 10, 9, 8, 7 or 5 (ng/mL)/(mg/kg). This is to say, the invention provides an opportunity to correctly prepare sustained release buprenorphine composition based on the pre-determined need of biopharmaceutical exposure.

In another aspect, the invention further provides a method to modulate the fluctuation of plasma level of buprenorphine over sustained release duration. The method relates to a tendency that the width of fluctuation inversely increases with Bup/OA ratio (wt/wt). Particularly, by dosing buprenorphine formulation with Bup/OA ratio at the level of 1, 2, 3, 5, 10 or 20 the peak-to-trough ratio (Cmax/Cmin or Cmax/Clast) may be at the level of no more than 20, 10, 7, 5 or 3. The invention provides an opportunity to correctly prepare sustained release buprenorphine composition based on the pre-determined need of plasma-level fluctuation.

An additional advantage provided by the buprenorphine formulation in this invention is that the AUC generally linearly and positively associated with the dose level, which is a favorable pharmacokinetic property, i.e., dose proportionality. This property enables more precise dosing plan before dose administration. Physician can select correct dose toward different patients with varied physical characteristics, severity of symptoms or response to buprenorphine.

Overall, the sustained release in the present invention relates to a simple method using fatty acid serving as drug delivery modulating agent. This method does not include highly viscous polymer and lipid depot to retard diffusion.

There is also no need to use chemical modification to covalently link fatty acid to drug, for dissolving bioactive in vegetable oil and formulate oil depot. Without being bound to theory, the fatty acid, with low hydrophilic-lipophilic balance (HLB) ranging from 1 to 3, may take advantage the amphiphilic property to modulate the solidification process and the size or morphology of drug crystal. Once the dosage is administrated, fatty acid may incorporate with buprenorphine to form a rather buprenorphine-rich hydrophobic droplet dispersed in a rather hydrophilic subcutaneous environment. Over the time that organic solvent diffuses away from buprenorphine composition, the buprenorphine rich droplet gradually solidify and turn into microsized buprenorphine crystal.

As used herein, the terms "treating," "treat," or "treatment" includes (i) preventing a pathologic condition (e.g., opioid use disorder (OUD)) from occurring (e.g., prophylaxis); (ii) inhibiting the pathologic condition (e.g., OUD) or arresting its development; and (iii) relieving the pathologic condition (e.g., relieving the symptoms associated with OUD).

EXAMPLES

The following examples illustrate the compositions and methods of the present invention. The following examples should not be considered as limitations, but should merely teach how to make the useful controlled release drug delivery compositions.

| MPB (v %) | Time (min) |
|---|---|
| 30 | 0 |
| 35 | 10 |
| 48 | 11 |
| 48 | 25 |
| 60 | 26 |
| 65 | 29 |
| 30 | 32 |
| 30 | 35 |

MPA + MPB = 100% during entire elution procedure.

Example 1. Buprenorphine Formulation Preparation and Stability Evaluation

The formulation preparation procedure mainly includes the preparation of vehicle, mixing of formulation and sterilization. Briefly, buprenorphine base solid was added into glass vials, weighing from 400 to 700 mg. Then about 5 grams vehicles comprising fatty acids (e.g., CPA and OA), pharmaceutical solvents (e.g., BA and BB) or a common parenteral ingredient, vegetable oil such as sesame oil (SO) were prepared as composition shown in Table 1, excluding the proportion of buprenorphine base. In which, ascorbic acid was dissolved in water before mixing with other vehicle components. The prepared vehicle weighed ranging from 1300 to 1600 mg was allocated to vials with buprenorphine solid. After moderate agitation overnight at room temperature, 2 grams of formulations complimentary to final composition can be recovered. Each formulation was subsequently aliquoted to vials sealed with rubber septa for stability study. The storage conditions include 25, 40, and 60° C.

TABLE 1

Buprenorphine formulations comprising fatty acid, organic solvent, vegetable oil or antioxidants

| Formulation | Bup (wt %) | CPA (wt %) | OA (wt %) | BA (wt %) | BB (wt %) | SO (wt %) | VC (wt %) | Water (wt %) | NMP (wt %) |
|---|---|---|---|---|---|---|---|---|---|
| FP-001 | 35 | 32.6 | | | 32 | | 0.1 | 0.3 | |
| FP-003 | 30 | 45 | | | | 24.6 | 0.1 | 0.3 | |
| FP-004 | 35 | 15.1 | | 49.5 | | | 0.1 | 0.3 | |
| FP-005 | 35 | 15 | | 50 | | | | | |
| FP-006 | 25 | | 30.5 | 27.6 | | 16.5 | 0.1 | 0.3 | |
| FP-007 | 30 | | 18 | 51.6 | | | 0.1 | 0.3 | |
| FP-008 | 20 | | | | | | | | 80 |

UPLC Method for Purity Evaluation.

The purity of buprenorphine was determined by the ratio of the peak area of parental buprenorphine divided by total peak areas of all distinguishable peaks of buprenorphine derivatives in the chromatogram. The UPLC was operated with following equipment and conditions: LC system: Shimadzu UPLC equipped with pumps (LC-30AD), autosampler (SIL-30AC), PDA (SPD-M30A) and column oven (CTO-20A); HPLC column: Waters ACQUITY UPLC BEH C18 1.7 um, 3.0×150 mm; Column oven temperature: 30° C.; HPLC elution and gradient: flow rate: 0.3 ml/min, mobile phase A (MPA): pH 4.5, potassium dihydrogen phosphate with 10% acetonitrile; mobile phase B (MPB): acetonitrile. The gradient is shown in Table below.

Color change in formulations was evaluated using UV-Vis spectroscopy at different temperature and over time, particularly pertaining with the absorbance at wavelength of 380 nm. In USP protocol 1061, the visible light is defined as the radiation with wavelength from 380 to 770 nm. For example, the absorbance at 380 nm (max Abs in visible wavelength) for these formulations was measured showed universally increase over time, even if VC was supplemented (Table 2). It appears that VC actually increases the absorbance at 380 nm in comparison to the formulation that does not contain VC (FP-004 vs FP-005) under the same condition. This indicates that VC alone may not be an effective color stabilizer.

TABLE 2

Absorbance at 380 nm of diluted samples and actual formulation

| Formulation No. | 25° C. -initial sample Abs380 nm | 25° C. -1 month formulation Abs380 nm | 40° C. -initial sample Abs380 nm | 40° C. -1 month formulation Abs380 nm |
|---|---|---|---|---|
| FP-001 | 0.005 | 0.392 | 0.007 | 0.52 |
| FP-003 | 0.003 | 0.264 | 0.006 | 0.464 |
| FP-004 | 0.012 | 0.92 | 0.02 | 1.568 |
| FP-005 | 0.006 | 0.472 | 0.012 | 0.976 |
| FP-006 | 0.007 | 0.536 | 0.008 | 0.648 |
| FP-007 | 0.01 | 0.832 | 0.015 | 1.2 |
| FP-008 | 0.004 | 0.32 | 0.011 | 0.856 |

The purity of buprenorphine formulation stored with 25, 40, and 60° C. was evaluated using UPLC with UV detection at 240 nm based on a European Pharmacopoeia (EP) method (07/2009: 1180) with minor modification. The operation parameters have been described in the paragraph of example UPLC method. The purity is presented as the percentage of peak area of buprenorphine divided by total peak area excluding vehicle peaks (Table 3 (a)).

The stability results showed that, at any storage conditions, the purity of buprenorphine in formulations containing VC remained higher than 98.68%. In contrast, in formulations without VC such as FP-005 and FP-008, the purity of buprenorphine was significantly deteriorated. Up to 4% to 8% more impurities were generated during 1-month at 60° C. for FP-005 and FP-008, respectively, comparing to the formulations containing VC. It was also found that the level of chemical degradation of buprenorphine was not simply correlated to the level of yellowing coloration (Table 3 (b)). FP-008 showed least color change by visual inspection among tested buprenorphine formulations but displayed the highest severity of degradation.

Example 2. Synergistic Effect of BA/OA on Bup Solubility

The solubility of buprenorphine in BA/OA mixture was tested at room temperature. The experimental procedure includes the addition of 400 mg buprenorphine base solid in about 600 mg vehicles. The vehicles include BA alone, OA alone and the BA/OA mixtures which were prepared with a series of increasing percentage of OA by weight. For example, 10% OA vehicle was composed of about 200 mg of OA and 1800 mg of BA, respectively. The complete composition of vehicle used in solubility study is shown as Table 4. After feeding of individual component, the mixtures were stirred for 3 days to approach the solubilization equilibrium at room temperature. Supernatant followed by high-speed centrifuge was collected and assayed by UPLC measurement. For UPLC analysis, the column and pumping system are Waters ACQUITY UPLC BEH C18 1.7 um, 3.0×150 mm and Shimadzu LC-30AD, respectively. The injected sample was isocratically eluted using 48% acetonitrile in water with 0.05% trifluoroacetic acid (TFA) and

TABLE 3

Stability of buprenorphine formulation at specified conditions.
(a) UPLC purity of buprenorphine and (b) apparent color (a)

| Formulation | Initial | 25° C. -1 mon | 40° C. -1 mon | 60° C. -1 mon |
|---|---|---|---|---|
| FP-001 | 99.40 | 99.29 | 99.22 | 99.40 |
| FP-003 | 98.95 | 99.09 | 99.04 | 99.05 |
| FP-004 | 99.70 | 98.98 | 98.86 | 99.38 |
| FP-005* | 99.71 | 98.68 | 97.43 | 94.60 |
| FP-006 | 99.40 | 98.87 | 99.27 | 99.36 |
| FP-007 | 99.69 | 99.57 | 98.66 | 99.05 |
| FP-008* | 99.71 | 98.60 | 95.72 | 90.35 |

The purity was calculated using the percentage of peak area of buprenorphine divided by total peak areas excluding peak area of vehicles.

*compositions without ascorbic acid (b)

| Formulation | Initial | 25° C. -1 mon | 40° C. -1 mon | 60° C. -1 mon |
|---|---|---|---|---|
| FP-001 | Colorless | Pale yellow | yellow | Yellow |
| FP-003 | Colorless | Pale yellow | Pale yellow | Yellow |
| FP-004 | Colorless | Amber yellow | Amber | Amber |
| FP-005 | Colorless | Amber yellow | Amber | Brown |
| FP-006 | Colorless | Pale yellow | Pale yellow | Amber |
| FP-007 | Colorless | Amber yellow | yellow | Amber |
| FP-008 | Colorless | Light yellow | Pale yellow | Yellow | column was located at 45° C. oven. The detection wavelength is 220 nm. As shown in Table 4, the results showed that the solubility of Bup increases with the OA content in the mixture, ranging from ~21% to ~36% by weight. BA/OA vehicles with 15 to 40 wt % OA provide enhanced solubility of buprenorphine, comparing it is in individual either OA or BA. Up to 50% of Bup may be achievable by using suitable combination of BA/OA. Higher solubility of Bup can reduce injection volume to achieve the same dose. A product with less injection volume should improve patient comfort and thus increase the compliance.

TABLE 4

Synergistic effect on Bup solubility in BA/OA combination vehicles

| Parameter | OA wt % | | | | | | | |
|---|---|---|---|---|---|---|---|---|
| | 0 | 5 | 10 | 15 | 18 | 30 | 40 | 100 |
| Solubility of buprenorphine | 21.2% | 22.5% | 25.4% | 30.7%* | 30.8%* | 33.1%* | 36.2%* | 27.7% |

*Bup solubility higher than it in either BA or OA individually.

Examples 3. Effect of Sulfur-Containing Antioxidants on Bup/BA/OA Formulation

Sulfur-containing antioxidants such as methionine (Met), monothioglycerol (MTG), cysteine (Cys), glutathione (Glu), sodium thioglycolate (STG) and lipoic acid (LipA) were included in the formulations for the stabilization of formulations as shown in Table 5. In which, formulation supplemented with VC and no antioxidant serve as controls. 2 grams of BA and 0.55 gram of OA were mixed rigorously to form clear BA/OA stock solution. Then, corresponding amount of antioxidant solution including EDTA, VC, Met, Cys, Glu and STG were pre-dissolved in water at 5 wt %, 20 wt %, 5 wt %, 10 wt %, 10 wt % and 40 wt %, respectively. MTG and LipA were pre-dissolved in BA at 40 wt % and 20 wt %, respectively. Accordingly, these antioxidant solutions were added in BA/OA vehicle at designed concentration. Then, 150 mg of buprenorphine base was weighed into a 2R vial and dissolved with 350 mg formerly described vehicle solution to produce buprenorphine formulations with 30 wt % buprenorphine content. 2R vials containing formulation was further crimped by rubber stopper and aluminum seal. Without further notice, all vehicles were firstly purged with nitrogen for 10 min and the overhead space of the 2R vial of formulations were then purged with nitrogen for additional 2 min. The formulation was compounded with agitation overnight at room temperature.

During stability test, all the formulations were incubated at 60° C. The color change was visually inspected. The purity of the buprenorphine was measured by UPLC as described in the paragraph of purity evaluation. The physical changes were examined by visual observation. As shown in FIG. 1, after incubating at 60° C. for 14 days, formulations with MTG and STG displayed milder coloration than that from other formulations. This color mitigation effect in Bup/BA/OA solution is effective in the presence of MTG at the concentration as low as 0.1% (referred to output of F1-3) after 14 day under stress condition.

TABLE 5

Color stabilization by antioxidant in buprenorphine formulation at 60° C. for 14 days

| | Formulation (30% Bup/15% OA/55% BA) | | |
|---|---|---|---|
| No. | Stabilizer | Con. (%) | Appearance |
| F1-1 | n/a | n/a | Yellow |
| F1-2 | VC/EDTA | 0.02/0.01 | Amber |
| F1-3 | MTG | 0.10% | Light pale yellow |

TABLE 5-continued

Color stabilization by antioxidant in buprenorphine formulation at 60° C. for 14 days

| | Formulation (30% Bup/15% OA/55% BA) | | |
|---|---|---|---|
| No. | Stabilizer | Con. (%) | Appearance |
| F1-4 | MTG | 0.50% | Light pale yellow |
| F1-5 | Met | 0.02% | Amber |
| F1-6 | LipA | 0.05% | Yellow |
| F1-7 | Glu | 0.01% | Yellow |
| F1-8 | Cys | 0.06% | Yellow |
| F1-9 | STG | 0.20% | Light pale yellow |

Example 4. Effect of Nitrogen Purging in Buprenorphine Formulation

The sample preparation was similar to procedure shown in Example 3. Briefly, BA/OA stock solution comprising 2 grams of BA and 0.55 gram of OA was prepared, followed by the supplement of corresponding amount of MTG solution (40 wt % MTG in BA) to reach the designed composition as shown in Table 6. During preparation procedure of F8-3 and F8-5, vehicle solutions were purged with nitrogen for 10 min (needle tip was emerged in solution). Then, 150 mg of buprenorphine base was weighed into a 2R vial and dissolved with 350 mg vehicle solution to produce buprenorphine formulations with 30 wt % buprenorphine content. The 2R vial containing buprenorphine formulation was further crimped by rubber stopper/aluminum seal in which overhead space were then filled with nitrogen for additional 2 min. On contrary, no nitrogen treatment was applied to vehicles and vials containing formulations for F8-6 and F8-7. The formulation was compounded with agitation overnight at room temperature. All formulations were subsequently incubated at 60° C. for 3 month.

The purity of the buprenorphine was measured by UPLC as the paragraph of purity evaluation, which is presented as the percentage of peak area of buprenorphine divided by total peak area excluding vehicle and BZ peaks. Similarly, BZ level is presented as the percentage of peak area of BZ divided by total peak area shown in chromatograms, excluding vehicle peak area. As shown in Table 6, nitrogen purge shows strong effect to minimize buprenorphine degradation significantly. However, nitrogen purging did not show any effect on the generation of BZ over a time period of 3 months at 60° C.

TABLE 6

Conditions of nitrogen purging effect

| No. | Formulation (30% Bup/15% OA/55% BA) | | | UPLC (3 M at 60° C.) | UPLC (3 M at 60° C.) | Nitrogen protection |
|---|---|---|---|---|---|---|
| | Stabilizer | Con. (%) | $N_2$ | BZ (%) | Purity (%) | Purity (%) |
| F8-3 | MTG | 0.6 | Yes | 4.39% | 97.68% | 6.78 |
| F8-5 | MTG | 1.0 | Yes | 4.86% | 98.28% | 6.89 |
| F8-6 | MTG | 1.0 | No | 4.28% | 91.39% | — |
| F8-7 | MTG | 0.6 | No | 4.88% | 90.90% | — |

Nitrogen protection is the difference of purity between buprenorphine formulations pre-treated nitrogen purging and those without nitrogen pretreatment, (e.g., Purity of F8-3 − Purity of F8-7 and Purity of F8-5 − Purity of F8-6)

Example 5. Effect of Combination of Antioxidants on Buprenorphine Formulation Both appearance and chemical stability are important for developing pharmaceutical products. In this example, the effect of both MTG and VC, either alone or in combination, on the stability of Bup in BA/OA formulations were investigated. Formulations were prepared with the procedure similar to the description in example 3. Briefly, BA/OA stock solution comprising 2 grams of BA and 0.55 gram of OA was prepared, followed by the supplement of corresponding amount of MTG solution (40 wt % MTG in BA) and VC (20 wt % VC in water) to reach the designed composition as shown in Table 7. All vehicle solutions were firstly purged with nitrogen for 10 min (needle tip was emerged in solution). Then, the 120 mg of buprenorphine base was weighed into a 2R vial and dissolved with 280 mg vehicle solution to prepare 30 wt % of buprenorphine formulation. 2R vial containing formulations were further crimped by rubber stopper/aluminum seal. Headspace in vials were then purged with nitrogen for another 2 min. The formulation was mixed with agitation overnight at room temperature. Formulations were subsequently incubated at 60° C. for 1 month. The appearance was evaluated by visual observation. The purity of buprenorphine was measured by UPLC, which is presented as the percentage of peak area of buprenorphine divided by total peak area excluding vehicle peaks. Similarly, BZ level is presented as the percentage of peak area of BZ divided by total peak area shown in chromatograms, excluding vehicle peak area. It was found that VC is effective in minimizing the generation of BZ, but not effective in preventing color change, while MTG is effective in suppressing color change, but caused significant generation of BZ. The combination of MTG and VC is very effective in suppressing color change and BZ generation. Therefore, the combination of two different type of stabilizers can be a very useful tool to maintain the stability of buprenorphine formulations.

TABLE 7

Effect of combination of antioxidants on buprenorphine formulation stored at 60° C. for one month

| No. | Formulation (30% Bup/15% OA/55% BA) | | | UPLC (1 M at 60° C.) | |
|---|---|---|---|---|---|
| | Stabilizer | Con. (%) | Color | Purity (%) | BZ (%) |
| F9-1 | n/a | n/a | Amber | 97.99 | 1.00 |
| F9-3 | VC | 0.02 | Amber | 99.75 | 0.13 |
| F9-4 | VC | 0.05 | Amber | 99.74 | 0.13 |

TABLE 7-continued

Effect of combination of antioxidants on buprenorphine formulation stored at 60° C. for one month

| No. | Formulation (30% Bup/15% OA/55% BA) | | | UPLC (1 M at 60° C.) | |
|---|---|---|---|---|---|
| | Stabilizer | Con. (%) | Color | Purity (%) | BZ (%) |
| F9-7 | MTG | 0.5 | Light pale yellow | 96.93 | 2.20 |
| F9-8 | MTG | 1.0 | Light pale yellow | 97.42 | 1.95 |
| F9-10 | MTG/VC | 0.5/0.02 | Light pale yellow | 99.29 | 0.58 |
| F9-11 | MTG/VC | 1/0.02 | Light pale yellow | 99.29 | 0.59 |
| F9-13 | MTG/VC | 0.5/0.05 | Light pale yellow | 99.39 | 0.48 |
| F9-14 | MTG/VC | 1/0.05 | Light pale yellow | 99.21 | 0.66 |

Example 6. Net Stabilization by Antioxidants in Buprenorphine Formulation

This example summarizes the modulation of antioxidant on net purity improvement (NPI) and net BZ generation (NBZ), which were difference of the buprenorphine purity increase and the BZ increase of studied formulation from the former stability parameters presented by sham (F9-1). Net stabilization result (calculated using results in Table 7) is listed in Table 8 and 9. NPI and NBZ were extracted to evaluate absolute capacity of antioxidant for preventing chemical degradation of buprenorphine and BA, respectively, involving three antioxidant treatments (VC, MTG and the combination) and two levels of supplement (0.02 and 0.05 wt % for VC; 0.1 and 0.5 wt % for MTG). Stability gain on NPI or NBZ is defined as the additional mitigation of buprenorphine or BA degradation in presence of VC-MTG combination antioxidant (column B in Table 8 and 9), comparing to the effect with assumption that VC and MTG functions completely independently, free from interrelationship (column A in Table 8 and 9). The degree of stability gain is positively associated to the benign interaction of VC and MTG on the stabilization of Bup/OA/BA formulations.

TABLE 8

Matrix of antioxidant effect on net purity improvement (NPI)

(a)

| NPI MTG (wt %) | VC (wt %) | | |
|---|---|---|---|
| | 0 | 0.02 | 0.05 |
| 0 | 0 | 1.76 | 1.75 |
| 0.5 | −1.06 | 1.3 | 1.4 |
| 1 | −0.57 | 1.3 | 1.22 |

(b)

| MTG (wt %) | NPI (VC) + NPI(MTG) A | NPI (VC + MTG) B | Stability gain by combination antioxidant B − A |
|---|---|---|---|
| 0.5 | 0.7 | 1.3 | 0.6 |
| 1 | 1.19 | 1.3 | 0.11 |

VC level is 0.02%.
The higher NPI suggests stronger purity improvement.
Composition of studied formulation is generally 30 wt % buprenorphine 15 wt % OA and 54~55 wt % BA.

TABLE 9

Matrix of antioxidant effect on net benzaldehyde (NBZ) generation (a)

| NBZ MTG (wt %) | VC (wt %) | | |
|---|---|---|---|
| | 0 | 0.02 | 0.05 |
| 0 | 0 | −0.87 | −0.87 |
| 0.5 | 1.2 | −0.42 | −0.52 |
| 1 | 0.95 | −0.41 | −0.34 |

(b)

| MTG (wt %) | NBZ (VC) + NBZ (MTG) A | NBZ (VC + MTG) B | Stability gain by combination antioxidant A − B |
|---|---|---|---|
| 0.5 | 0.33 | −0.42 | 0.75 |
| 1 | 0.08 | −0.41 | 0.49 |

VC level is 0.02%.
Lower NBZ suggests stronger suppression on BZ generation.
Composition of studied formulation is generally 30 wt % buprenorphine 15 wt % OA and 54~55 wt % BA.

Example 7. Autoclavable Buprenorphine Formulation

The formulation preparation procedure mainly includes the preparation of vehicle, mixing of formulation and sterilization. First, vehicles were prepared by mixing liquid ingredients such as 20% (w/w) VC aqueous solution, liquid fatty acid, solvent and antioxidants to produce 10 grams of vehicle in 20 ml vials. The clear admixture vehicle was then purged with nitrogen for 5 minutes (the needle tip is emerged into vehicle). Buprenorphine base and vehicles complementary to composition were added and weighed in the glass vial to prepare ~3 grams of formulation. All vials with feeding ingredients were crimped with aluminum cap and filled with nitrogen for 1 min to ensure headspace was under nitrogen protection. Then buprenorphine solid and vehicle was mixed and agitated at room temperature for 2 to 4 hours to produce clear buprenorphine solution. The composition of the formulations is shown in Table 10.

The recovered formulation was thus filled into a 1 mL long glass prefillable syringe (BD hypak staked-needle syringe), coupled with 29G needles, from the front and sealed with a fluoropolymer-coated butyl-rubber plunger (West 2340 4432/50 B2-40 Westar® RU). The filling quantity is about 300 mg of formulation F10-1. Formulation-filled staked needle syringes with needle shield-capped was thus autoclaved at 121° C. for 30 minutes. No leak of formulation or plunger dislocation was observed after autoclaving. These packed formulations were subsequently stored horizontally in various storage conditions. During stability study, the pH of formulation is measured after 10-fold dilution with de-ionized water at room temperature; purity was calculated using the percentage of peak area of buprenorphine divided by total peak areas excluding peaks generated by vehicle; color is rated by visual inspection. Generally, all stability parameters are similar to the initial conditions (Table 11).

TABLE 10

Buprenorphine composition with autoclave sterilization

| Formulation | Composition (wt %) |
|---|---|
| F10-1 | Bup/OA/BA/VC/MTG/H$_2$O (25/9/65.6/0.02/0.3/0.08) |

TABLE 11

Stability parameters of autoclaved buprenorphine formulation

| Formulation F10-1 | Initial* | 40° C. -1 m | 60° C. -1 m | 25° C. -3 m | 40° C. -3 m |
|---|---|---|---|---|---|
| pH | 6.47 | 6.43 | 6.56 | 6.56 | 6.60 |
| Purity | 99.88 | 99.85 | 99.79 | 99.86 | 99.84 |
| Color | colorless | colorless | Pale yellow | colorless | Light pale yellow |

*Initial conditions were evaluated at room temperature, 1 hour after autoclave.
The pH of formulation is measured after 10-fold dilution with de-ionized water at room temperature.
The purity was calculated using the percentage of peak area of buprenorphine divided by total peak areas excluding peaks given by vehicles.

Example 8. Buprenorphine Formulation Showing Enhanced Bio-Absorption

Two buprenorphine formulations comprising fatty acid and organic solvent, (FP-006 and 007) and one buprenorphine-NMP control, FP-008, were prepared for in vivo pharmacokinetic (PK) studies. The composition was identical to those listed in Table 1. The formulation preparation procedure except for FP-008 mainly includes the preparation of vehicle, mixing of formulation and sterilization. First, vehicles were prepared by mixing liquid ingredients such as 20% (w/w) VC aqueous solution, fatty acid (OA) and solvent to produce 10 grams of vehicle in 20 ml vials. The clear admixture vehicle was then purged with nitrogen for 5 minutes (the needle tip is emerged into vehicle). Buprenorphine base and vehicles complementary to composition were added and weighed in the glass vial to prepare ~3 grams of formulation. All vials containing formulations were crimped with aluminum cap and filled with nitrogen for 1 min to ensure headspace was under nitrogen protection. Then solid and vehicle was mixed at room temperature overnight to produce clear solution. FP-008 was prepared by directly mixing of Bup base and NMP solvent. With 2 hours of agitation, clear solution was obtained. All tested articles were sterilized using 0.22 μm filtration, followed by filling in aluminum-crimped vials under nitrogen protection.

PK studies of test formulations were conducted in male Sprague-Dawley rats, with a body weight of ~300 grams. For each test formulation, five rats were administrated subcutaneously at the level of 75 mg/kg through the site of dorsal thoracic. Blood samples were collected by bleeding the lateral veins with EDTA disodium as anti-coagulant. Collected blood samples were centrifuged for 15 min at 1000×g within 60 minutes after blood collection. The plasma samples were stored in a freezer at temperature below −60° C. Buprenorphine plasma level in samples was measured using LC-MS/MS. This in vivo study procedure was also used in other examples for animal studies.

The PK profiles are plotted in FIG. 2. PK parameters relevant to sustained release, including area-under-curve (n-AUC) (normalized by dose level), peak-to-trough (P/T) ratio and a combinatory factor, the product of former both parameters, are accordingly extracted and summarized in Table 12. Particularly, the combinatory factor considers both the bioavailability and controlled release, which serve as a bi-functional indicator evaluating the potent of sustained release. The PK results suggest both Bup/OA/BA formulations, FP-006 and FP-007, were able to achieve at least one month sustained release. Furthermore, FP-007 shows highest combinatorial sustained release factor (n-AUC/(P/T)). Comparing to formulation without fatty acids (FP-008), Bup/OA/BA formulations demonstrated 75% to 120% higher exposure in vivo.

In another example, one Bup/OA/BA formulation and one Bup PLGA formulation were prepared for in vivo pharmacokinetic (PK) studies. The compositions were listed in Table 13. The preparation of procedure of FP-009 is similar to the procedure, as described in the procedure for FP-006, briefly including antioxidant solution preparation, vehicle preparation, formulation compounding and sterile filtration. The preparation procedure of FP-010 included the dissolving of PLGA (Evonik, RG502H, MW=7~17 kD) in NMP, followed with the dissolving of solid buprenorphine base in previously prepared polymeric vehicles. Clear viscous FP-010 was accordingly conducted with sterile filtration and filled in crimped vial with nitrogen protection.

TABLE 13

| Composition of Bup formulations for in vivo PK studies | |
|---|---|
| Formulation | Composition (%) |
| FP-009 | Bup/OA/BAA/C/MTG/H$_2$O (24/7/68.8/0.02/0.1/0.08) |
| FP-010 | Bup/PLGA/NMP (18/32.8/49.2) |

This in vivo PK profiles were conducted with subtle modification. The identical parameters include route of administration (SC), dose level (75 mg/kg) and treated animals (SD male rats). In this study, six replicates were dosed with both formulations. The PK profiles (FIG. 3) clearly demonstrated enhanced bio-absorption in vivo demonstrated by FP-009, a Bup/OA/BA formulation, compared with FP-010, a typical polymeric buprenorphine formulation. Quantitative PK parameters further suggest, with comparable $C_{max}$, the AUC of FP-009 was more than double of AUC performed by FP-010. In addition, peak-to-trough ratio (PTR) of FP-009 was 40% less than PTR of FP-010, suggesting narrower fluctuation demonstrated by Bup/OA/BA formulation, with no aid from polymeric controlled release material (Table 14). This allows producing a simpler formulation with simpler and cost effective manufacturing process.

TABLE 14

| PK parameters of Bup/OA/BA and Bup/PLGA/NMP formulations | | |
|---|---|---|
| Parameters | FP-009 | FP-010 |
| n-Cmax (ng/mL)/(mg/kg) | 0.84 | 0.73 |
| Peak/Trough, 28 days (P/T) | 4.12 | 7.36 |
| n-AUC, (day × ng/mL)/(mg/kg) | 10.32 | 4.83 | n: dose-normalized.
P/T = $C_{max}/C_{28\,d}$

TABLE 12

| PK parameters of the buprenorphine formulation in rat | | | |
|---|---|---|---|
| Formulation | n-AUC, 28 days (day × ng/mL)/(mg/kg) | Peak/Trough, 28 days (P/T) | n-AUC/(P/T), 28 days (day × ng/mL)/(mg/kg) |
| FP-006 | 9.8 | 11.5 | 0.9 |
| FP-007 | 12.4 | 8.3 | 1.5 |
| FP-008 | 5.6 | 4.7 | 1.2 | n-AUC stands for dose-normalized area-under-curve (N = 5).
P/T = $C_{max}/C_{28\,d}$

Examples 9. Controllable PK Properties of Buprenorphine Formulation

The formulation preparation procedure mainly includes the preparation of vehicle, mixing of formulation and sterilization, as described in example 8. Briefly, vehicles were prepared by mixing liquid ingredients such as 20% (w/w) VC aqueous solution, liquid fatty acid, solvent and other antioxidants to produce 10 grams of vehicle in 20 ml vials. The clear admixture vehicle was then purged with nitrogen for 5 minutes (the needle tip is emerged into vehicle). Buprenorphine base and vehicles were weighed and added in the glass vial, crimped with aluminum cap and filled with nitrogen for 1 min to ensure headspace was under nitrogen protection. Then buprenorphine base and vehicles were mixed and agitated at room temperature overnight to obtain a clear solution. All test articles were sterilized using 0.22 μm filtration, followed by filling in aluminum-crimped vials with nitrogen protection. The composition of formulations is shown in Table 15.

TABLE 15

Composition of buprenorphine formulations in PK studies

| Formulation | Bup (%) | OA (%) | BA (%) | VC (%) |
|---|---|---|---|---|
| F-SC-1 | 30 | 18 | 52 | 0.02 |
| F-SC-2 | 25 | 5 | 70 | 0.02 |
| F-SC-5 | 30 | 15 | 55 | 0.02 |

28-day PK profiles in rats dosed with buprenorphine formulations with OA/BA vehicle, with OA content ranging from 5 to 18% were obtained. The experimental method including administration, dose level and evaluation of blood samples is identical as the procedure described in example 8. Briefly, 75 mg/kg dose level (F-SC-1 and 2) was subcutaneously administrated in rats (N=5). Buprenorphine plasma level was analyzed using LC/MS/MS. The PK profiles were illustrated in FIG. 4. All the formulations show good sustained release PK profiles over a period of at least one month.

TABLE 15

PK parameters of Bup/OA/BA formulation

| Parameters | F-SC-1 | F-SC-2 |
|---|---|---|
| n-Cmax (ng/mL)/(mg/kg) | 0.89 | 0.58 |
| Peak/Trough, 28 days (P/T) | 5.08 | 7.35 |
| n-AUC, (day × ng/mL)/(mg/kg) | 11.69 | 7.25 | n: dose-normalized.
P/T = $C_{max}/C_{28\,d}$

In dose proportionality study, F-SC-5 was dosed subcutaneously at levels of 25, 75 and 150 mg/kg, respectively. Buprenorphine plasma level was evaluated using LC MS/MS. The plot of the area-under-curve (N=5) within 28 days postdose ($AUC_{0-28\,days}$) against dose levels (25, 75 to 150 mg Bup/kg rat) was shown in FIG. 6. The $AUC_{0-28}$ days is highly positively associated with dose levels with very good dose proportionality.

Example 10. Effect of Light on the Formation of Benzaldehyde

In this example, several stabilizer or combinations of MTG, EDTA, and VC, are included in both BA only and BA/OA combination solution. In general, the corresponding amount of antioxidant (% w/w) were added into BA (1.8 g) solution or BA/OA (1.8 g/0.49 g) solution. The mixture was further mixed well by vortex and incubated under pre-defined conditions. The % BZ was determined by UPLC, calculated by the percentage of BZ peak area over BA peak area.

As shown in Table 16, after exposure with UV light for about one hour, the % BZ increases significantly in both BA only and BA/OA combination solutions, especially with the presence of MTG. MTG is a common antioxidant to prevent oxidation reactions between compound and free radicals. It is quite surprising that MTG did not prevent the oxidation of BA to BZ. However, when MTG was combined with VC, the formation of BZ after exposure with UV light (F3-6, 8 and 11) was significantly decreased.

TABLE 16

Effect of UV light on BZ formation

| Vehicle | MTG % | VC % | EDTA % | BA only % BZ D 0 | BA only % BZ After UV | BA/OA[1] % BZ[2] D 0 | BA/OA[1] % BZ[2] After UV |
|---|---|---|---|---|---|---|---|
| F3-1 | 0 | 0 | 0 | 0.25% | 0.81% | 0.25% | 0.63% |
| F3-2 | 0.1 | 0 | 0 | 0.31% | 3.85% | 0.31% | 5.52% |
| F3-3 | 0.5 | 0 | 0 | 0.37% | 8.12% | 0.37% | 7.40% |
| F3-6 | 0.5 | 0.02 | 0 | 0.32% | 3.46% | 0.32% | 1.23% |
| F3-8 | 0.5 | 0.04 | 0 | 0.35% | 2.43% | 0.35% | 1.19% |
| F3-11 | 0.5 | 0.04 | 0.01 | 0.33% | 2.33% | 0.33% | 1.01% |

[1] OA = 15%;
[2] BZ calculated from peak area of BZ divided by peak area of BA

All publications, patents, and patent documents are incorporated by reference herein, as though individually incorporated by reference. The invention should now be illustrated with the following non-limiting examples.

What is claimed is:

1. An injectable pharmaceutical composition comprising 1) at least 1 wt % of buprenorphine in form of free base or a pharmaceutically acceptable salt thereof; 2) benzyl alcohol (BA); 3) an oleic acid; and 4) a combination of 0.1% to 2.0% monothioglycerol (MTG) by weight and 0.01% to 0.05% ascorbic acid (VC) by weight, wherein color of the injectable pharmaceutical composition remains colorless to pale yellow after having been stored at 60° C. for 3 months and viscosity of injectable pharmaceutical composition is no more than 1000 Centipoise (cPs).

2. The injectable pharmaceutical composition of claim 1 comprising buprenorphine in form of the free base.

3. The injectable pharmaceutical composition of claim 1 comprising 1 wt % to 40 wt % buprenorphine in form of free base or a pharmaceutically acceptable salt thereof.

4. The injectable pharmaceutical composition of claim 1 comprising 5 wt % to 35 wt % buprenorphine in form of free base or a pharmaceutically acceptable salt thereof.

5. The injectable pharmaceutical composition of claim 1 comprising 10 wt % to 30 wt % buprenorphine in form of free base or a pharmaceutically acceptable salt thereof.

6. The injectable pharmaceutical composition of claim 1 comprising no greater than 40 wt % oleic acid.

7. The injectable pharmaceutical composition of claim 1 comprising 1 wt % to 30 wt % oleic acid.

8. The injectable pharmaceutical composition of claim 1 comprising 3 wt % to 10 wt % oleic acid.

9. The injectable pharmaceutical composition of claim 1 comprising 10 wt % to 90 wt % benzyl alcohol.

10. The injectable pharmaceutical composition of claim 1 comprising 30 wt % to 80 wt % benzyl alcohol.

* * * * *